United States Patent
Lockwood, Jr.

(10) Patent No.: US 7,114,495 B2
(45) Date of Patent: Oct. 3, 2006

(54) NASAL STRIP WITH VARIABLE SPRING RATE

(75) Inventor: Hanford N. Lockwood, Jr., San Mateo, CA (US)

(73) Assignee: Silver Eagle Labs Inc., Carson City, NV (US)

(*) Notice: Subject to any disclaimer, the term of this patent is extended or adjusted under 35 U.S.C. 154(b) by 0 days.

(21) Appl. No.: 10/839,879

(22) Filed: May 5, 2004

(65) Prior Publication Data

US 2005/0247317 A1    Nov. 10, 2005

(51) Int. Cl.
    *A61M 15/00*    (2006.01)

(52) U.S. Cl. ............................ 128/200.24; 128/206.11; 606/199; 606/204.45

(58) Field of Classification Search .......... 128/200.24, 128/206.11, 207.18; 606/199, 204.45
See application file for complete search history.

(56) References Cited

U.S. PATENT DOCUMENTS

| | | | | |
|---|---|---|---|---|
| 5,476,091 A * | 12/1995 | Johnson | .................. | 128/200.24 |
| 5,479,944 A | 1/1996 | Petruson | | |
| 5,533,499 A * | 7/1996 | Johnson | .................. | 128/200.24 |
| 5,546,929 A * | 8/1996 | Muchin | .................. | 128/200.24 |
| RE35,408 E * | 12/1996 | Petruson | ..................... | 128/858 |
| 5,611,333 A * | 3/1997 | Johnson | .................. | 128/200.24 |
| 5,653,224 A * | 8/1997 | Johnson | .................. | 128/200.24 |
| 5,706,800 A * | 1/1998 | Cronk et al. | ........... | 128/200.24 |
| 5,718,224 A * | 2/1998 | Muchin | .................. | 128/200.24 |
| 5,769,089 A * | 6/1998 | Hand et al. | .................. | 128/858 |
| 5,890,486 A * | 4/1999 | Mitra et al. | ............. | 128/200.24 |
| 5,913,873 A * | 6/1999 | Blach et al. | ........... | 606/204.45 |
| 5,931,854 A * | 8/1999 | Dillon | .................... | 606/204.45 |
| 5,957,126 A * | 9/1999 | Neeser | .................. | 128/200.24 |
| 6,006,746 A * | 12/1999 | Karell | .................... | 128/200.24 |
| 6,029,658 A * | 2/2000 | De Voss | ................. | 128/200.24 |
| 6,058,931 A * | 5/2000 | Muchin | .................. | 128/200.24 |
| 6,065,470 A * | 5/2000 | Van Cromvoirt et al. | ...................... | 128/200.24 |
| 6,098,616 A * | 8/2000 | Lundy et al. | ........... | 128/200.24 |
| 6,244,265 B1 * | 6/2001 | Cronk et al. | ........... | 128/200.24 |
| 6,276,360 B1 * | 8/2001 | Cronk et al. | ........... | 128/200.24 |
| 6,318,362 B1 * | 11/2001 | Johnson | .................. | 128/200.24 |
| 6,375,667 B1 * | 4/2002 | Ruch | .......................... | 606/199 |
| 6,453,901 B1 * | 9/2002 | Ierulli | .................... | 128/200.24 |
| 6,550,474 B1 * | 4/2003 | Anderson et al. | ...... | 128/200.24 |
| 6,694,970 B1 * | 2/2004 | Spinelli et al. | ........ | 128/200.24 |
| 6,769,428 B1 * | 8/2004 | Cronk et al. | ........... | 128/200.24 |
| 6,769,429 B1 * | 8/2004 | Benetti | .................. | 128/200.24 |

FOREIGN PATENT DOCUMENTS

ES    289561    10/1985

* cited by examiner

*Primary Examiner*—Aaron J. Lewis
(74) *Attorney, Agent, or Firm*—Townsend and Townsend and Crew LLP

(57) ABSTRACT

A nasal dilator capable of introducing separating stresses in nasal outer wall tissues has a truss of a single body with a resilient member secured therein and a pair of spaced-apart end surfaces which, when forced toward one another from initial positions to substantially reduce direct spacing therebetween by a spacing reducing force external to said truss, results in restoring forces in the truss tending to return to the original direct spacing between the end surfaces. A resilient member, which is symmetrical with respect to a centerline of the truss that is perpendicular to the long axis of the truss, has a spring rate which continuously diminishes from the centerline to the end surfaces. An adhesive on the end surfaces adhesively engages exposed surfaces of nasal outer wall tissues sufficiently to keep the truss attached to the nasal wall surfaces while subjecting them to the restoring forces.

21 Claims, 3 Drawing Sheets

NASAL STRIP WITH VARIABLE SPRING RATE

BACKGROUND OF THE INVENTION

This invention relates to an improvement to the design of a nasal dilator that is described in Spanish Patent No. 289,561 for Orthopaedic Adhesive granted to Miguel Angel Aviles Iriarti on 15 Sep. 1986. The Iriarti patent describes two designs of a nasal dilator. The first consists of a resilient band which has an adhesive on the bottom side and sufficient length so that when the center of the resilient band is bent over the bridge of the nose, each end is attached to the soft tissue on the lateral wall of the nasal passage. The adhesive can be applied as part of the back of the resilient band or applied directly to the skin prior to the application of the resilient band.

The second design described in the Iriarti patent shows a soft fabric cover with an adhesive on the bottom side which is larger than the resilient band. The resilient band is centered on the bottom of the soft fabric cover and attached to the adhesive. The center of the two-piece nasal dilator is bent over the bridge of the nose, and each end is attached to the soft tissue on the lateral wall of the nasal passage using the adhesive on the soft fabric cover that extends beyond the edge of the resilient band.

The mechanical forces generated by bending the resilient band from its initial planar state to its deformed state with the ends in contact with the lateral wall of the nasal passages result in forces tending to pull out on the lateral wall tissues which stabilize the walls of the nasal passages during breathing. The forces generated by the resilient band may be greater than the available strength of the adhesive which is located in the border of the soft fabric cover that extends beyond the resilient band as discussed in the second Iriarti design. One skilled in the art could combine the two Iriarti designs and add additional adhesive to the bottom of the resilient band which is attached to the bottom of the soft fabric cover and increase the ability of the nasal dilator to resist the mechanical forces generated by the resilient band.

The present invention is an improvement to the nasal dilator design disclosed in the Iriarti patent because it has a resilient band which has a variable spring rate that decreases from the point where the resilient band crosses the bridge of the nose to the point where the resilient band terminates at the lateral wall of the nasal passage.

The present invention also has a concave indent on one side of the dilator and a convex protrusion on the opposite side of the dilator at the center of the bridge of the nose to indicate to the user the proper orientation of the dilator when it is in use.

Another improvement to the Iriarti design is the use of a soft fabric cushion with adhesive on both sides to prevent the resilient band from coming in contact with the user's skin. This soft fabric cushion is the same size as the top soft fabric cover.

Blockage of the nasal passages from swelling due to allergies, colds and physical deformities can lead to breathing difficulty and discomfort. The nasal passages have mucus membranes which condition the air in the nasal passages prior to its arrival in the lungs. If the nasal passages are constricted due to swelling or minor deformities then the alternative is to breathe through the mouth. This means that the air bypasses the mucus membranes, losing the conditioning effects and causing irritation in the throat and lungs. At night, restrictions to breathing through the nasal passages can lead to snoring and/or sleep disturbances. In some cases, the restricted air supply can cause sleep problems brought on by a lack of oxygen.

For people with chronic blockages in the nasal passages, the alternative to correct the problem has been expensive surgery or medication. People with minor deformities and breathing problems brought on by swelling of the walls of the nasal passageways have been turning to various products fitted in or on the nose which claim to open the nasal passages.

The structure of the nose limits the options available for the design of nasal dilators. The nose terminates at the nostril, which has a slightly expanded volume immediately above it known as the vestibule. Above the vestibule, the nasal passage becomes restricted at a point called the nasal valve. At the nasal valve, the external wall of the nose consists of soft skin known as the lateral wall, which will deform with air pressure changes induced within the nasal passage during the breathing cycles. Above the nasal valve the nasal passage opens up to a cavity with turbinates over the top of the palate and turns downward to join the passage from the mouth to the throat.

The external structure of the nose consists of a skin covering over the nasal bones which are part of the skull. This gives the top of the nose a rigid structure at its base. Beyond the rigid nose bones, there is thin cartilage under the skin which is attached to the septum, which in turn contributes to the outside shape of the nose. The septum forms the wall between the two nostrils and may, if it is crooked, contribute to breathing problems.

As an alternative to surgery, the structure of the nose and the current art leave two alternatives for the design of nasal dilators. One alternative is the type of dilator that consists of some type of tube or structure which can be inserted into the nasal passage to hold it in the open position allowing the free passage of air. The disadvantage to this design is that the dilator structure covers up the mucus membranes which condition the air. Also dilators of this design are uncomfortable and can irritate the walls of the nasal passage.

The second alternative is a dilator design as taught by Iriarti where each end that attaches to the external lateral wall of each of the nasal passages has some type of resilient means connecting the ends for developing an external pulling force on the lateral wall causing it to open the nasal passage. This design has the advantage over the first alternative because the nasal passages are not disturbed by an internal insert. This design has limited control over the resilient force on the lateral wall of each of the nasal passages, and the resilient members crossing over the bridge of the nose can cause discomfort.

The present invention is an improvement over the Iriarti design because it redistributes the lifting forces within the resilient band by modifying the spring rate, so that they can provide optimum lift on the lateral walls of the nasal passage and maximum comfort to the user.

The prior art that comes closest to the present invention is nasal dilators with some means for adjusting the spring rate of the resilient band in the nasal dilator. The first is U.S. Pat. No. 5,476,091 to Johnson, which shows two parallel resilient bands of constant width and constant thickness which cross over the bridge of the nose and terminate at the outer wall of each nasal passage. The Johnson patent shows a plurality of notches cut into the top of each end of the resilient band to reduce the spring rate, which in turn prevents the end of the resilient band from peeling away from the skin. Each notch is a single point reduction of the spring rate with the spring rate reduction determined by the depth of the notch.

The second U.S. Pat. No. 5,479,944 to Petruson and the third U.S. Pat. No. Re 35,408 to Petruson cover the same nasal dilator design. In these patents, the nasal dilator is a one-piece molded plastic strip, the ends of which carry tabs for insertion into the nostrils.

The fourth U.S. Pat. No. 5,611,333 to Johnson shows the same concept of single point reduction in the spring rate of the resilient band using the notches shown in U.S. Pat. No. 5,476,091 mentioned above. In addition this patent shows other designs for the resilient band with either holes or slots which are located at the ends of the resilient bands and are designed to reduce the spring rate at a single point to prevent the end of the resilient band from peeling away from the skin.

The fifth U.S. Pat. No. 6,029,658 to Voss shows a beam-shaped resilient band which extends from one side of the user's nose across the bridge of the nose to the other side of the nose. The resilient band is made of plastic and has a varying thickness and width over the entire span. The resilient band exhibits a rigidity increase from the center towards the two respective ends which attach to the sides of the user's nose, which is the exact opposite of what is attained with the present invention.

The sixth U.S. Pat. No. 6,453,901 to Ierulli shows several nasal strip designs where the cover member extends beyond the perimeter of the spring member, including one embodiment in which the strip has some degree of variation in the spring force over a portion of the length of the strip.

There are many other patents describing nasal dilator designs, but none of them teach the advantage of using a resilient band with a means for varying the spring rate to improve the performance of the nasal dilator or reduce the peel forces at the ends of the strip.

SUMMARY OF THE INVENTION

The object of this invention is to provide a nasal dilator which exhibits improved performance relative to the nasal dilator described in the Spanish Patent No. 289,561 for Orthopaedic Adhesive granted to Iriarti. The Iriarti patent shows two nasal dilator designs. The first design consists of a resilient band with adhesive on the bottom side which crosses over the bridge of the nose and has two ends each of which terminates at the lateral walls of the nasal passages. The resilient band pulls out the lateral walls as it attempts to return to its natural planar state.

The second design consists of a soft fabric cover with adhesive on the bottom side which is larger than the resilient band. The resilient band is attached to the adhesive in the center of the bottom of the soft fabric cover. The dilator assembly is centered on the bridge of the nose, and the ends are each bent until they are in contact with the lateral walls of the nasal passages. The surface of the soft fabric cover that extends beyond the borders of the resilient band has the adhesive which holds the dilator on the skin of the nose. As in the first design, the resilient band pulls out the lateral walls as it attempts to return to its natural planar state.

Combining the two Iriarti designs for a nasal dilator improves the performance of the dilator, because greater adhesive surface is available to hold the dilator in place on the user's nose and overcome the stresses contained in the resilient band. The improvements to the Iriarti design which are part of this invention are intended to further improve the performance and comfort of the dilator.

An improvement to the Iriarti dilator that is according to the present invention is a change in the configuration of the resilient band to reduce the width gradually from the center of the resilient band towards each end in a way that gradually reduces the spring rate of the resilient band. The thickness of the resilient band remains constant over its entire length, which simplifies the structure while keeping costs low.

Another improvement provided by the present invention is the provision of a concave indent on one side of the dilator and a convex protrusion on the opposite side of the dilator at the center of the dilator where it crosses the bridge of the user's nose. The indent and protrusion assist the user in properly orienting the dilator so it can be properly positioned on the user's nose for optimum performance.

Another improvement of the present invention, particularly over the Iriarti dilator, is the addition of a bottom soft fabric cover which is of the same size and shape as the top soft fabric cover and has adhesive on both sides. The bottom soft fabric cover prevents the resilient band from contacting the user's skin, so the resilient band is in contact with the adhesive on the top surface while the adhesive on the bottom surface of the bottom soft fabric cover attaches the dilator to the skin on the user's nose.

Another improvement of the present invention is the use of transparent materials for the top soft fabric cover, the resilient band, and the bottom fabric cover. The normal color for the top soft fabric cover is tan; however, for sports applications the cover may be black or some other dark color.

The improvements summarized above enhance the performance of the dilator and make the dilator more comfortable for the user as compared to prior art dilators in general and the Iriarti dilator in particular.

BRIEF DESCRIPTION OF THE DRAWINGS

The unique advantages of the present invention will become apparent to one skilled in the art upon reading the following specification and by reference to the following drawings.

DESCRIPTION OF THE PREFERRED EMBODIMENTS

The specific improvements provided by this invention over the nasal dilator design described in Spanish Patent No. 289,561 to Iriarti are best seen in the attached drawings.

Figure 1:
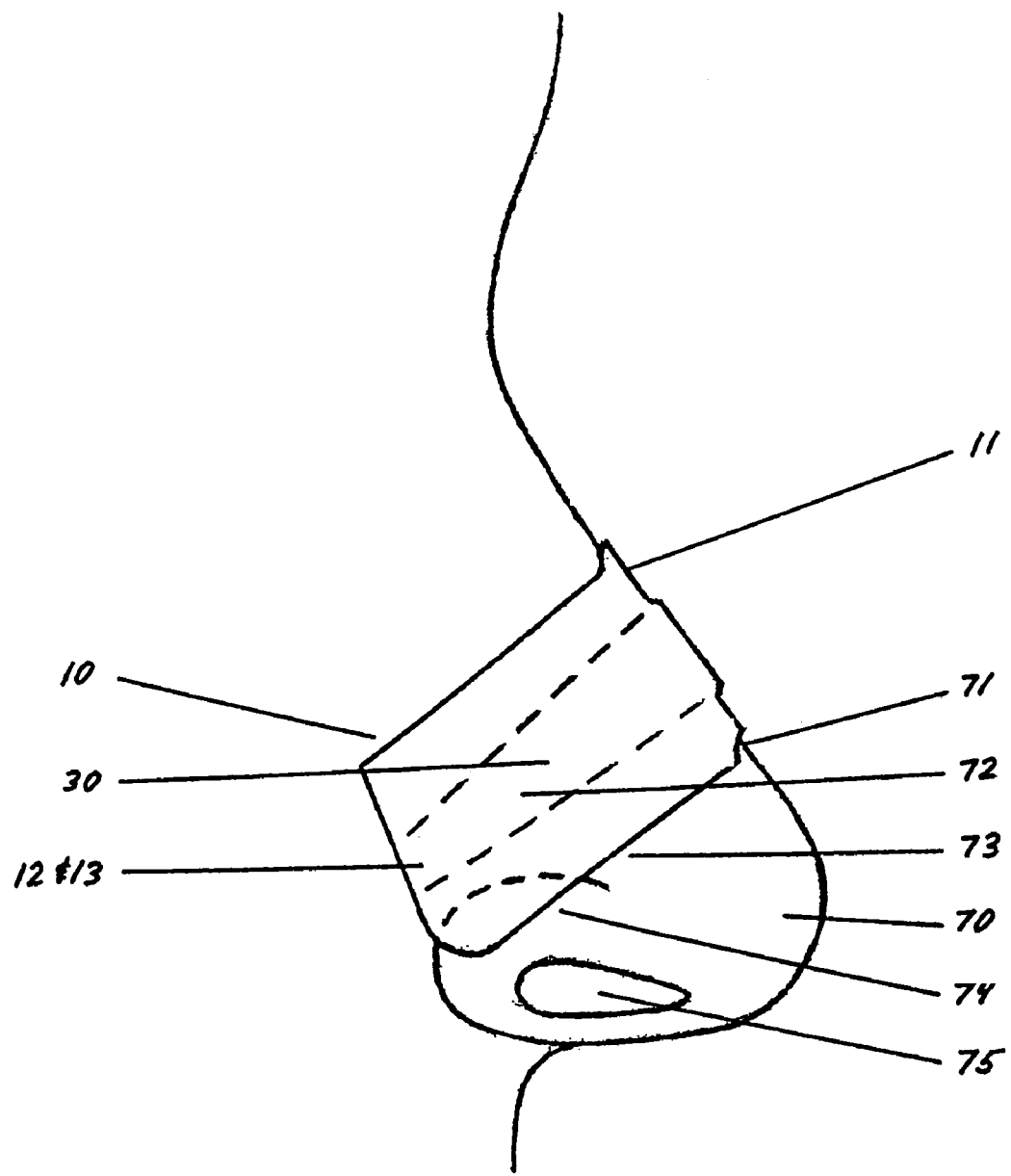
FIG. 1 is a side view of the dilator on the nose.

FIG. 1 shows the new nasal dilator 10 mounted on the nose 70 of the user. The nasal dilator 10 is designed so that the center 11 of the nasal dilator 10 is bent over the bridge 71 of the nose 70 and each end 12 and 13 of the nasal dilator 10 is positioned over the lateral wall 72 of the nose 70.

The lateral wall 72 of the nasal passage 75 is located in the soft tissue 73 above the nostril flare 74, which in turn is adjacent to the entrance of the nasal passage 75. When the nasal dilator 10 which contains a resilient band 30 is deformed from its normally planar state by being bent over the bridge 71 of the nose 70, the ends 12 and 13 which are attached to the lateral wall 72 of the nasal passage 75 tend to pull on the lateral wall 72 in a way that opens the nasal passage 75 and improves the air flow through the nasal passages 75 during breathing. The Iriarti patent describes two designs of a nasal dilator which can perform the function of dilating the lateral walls 72 of the nasal passages 75.

This invention shows improvements to the Iriarti nasal dilator design that improve the performance of the nasal dilator 10, make the nasal dilator 10 easier to use, and improve the comfort of the nasal dilator 10 when it is in use on the user's nose 70.

Figure 2:
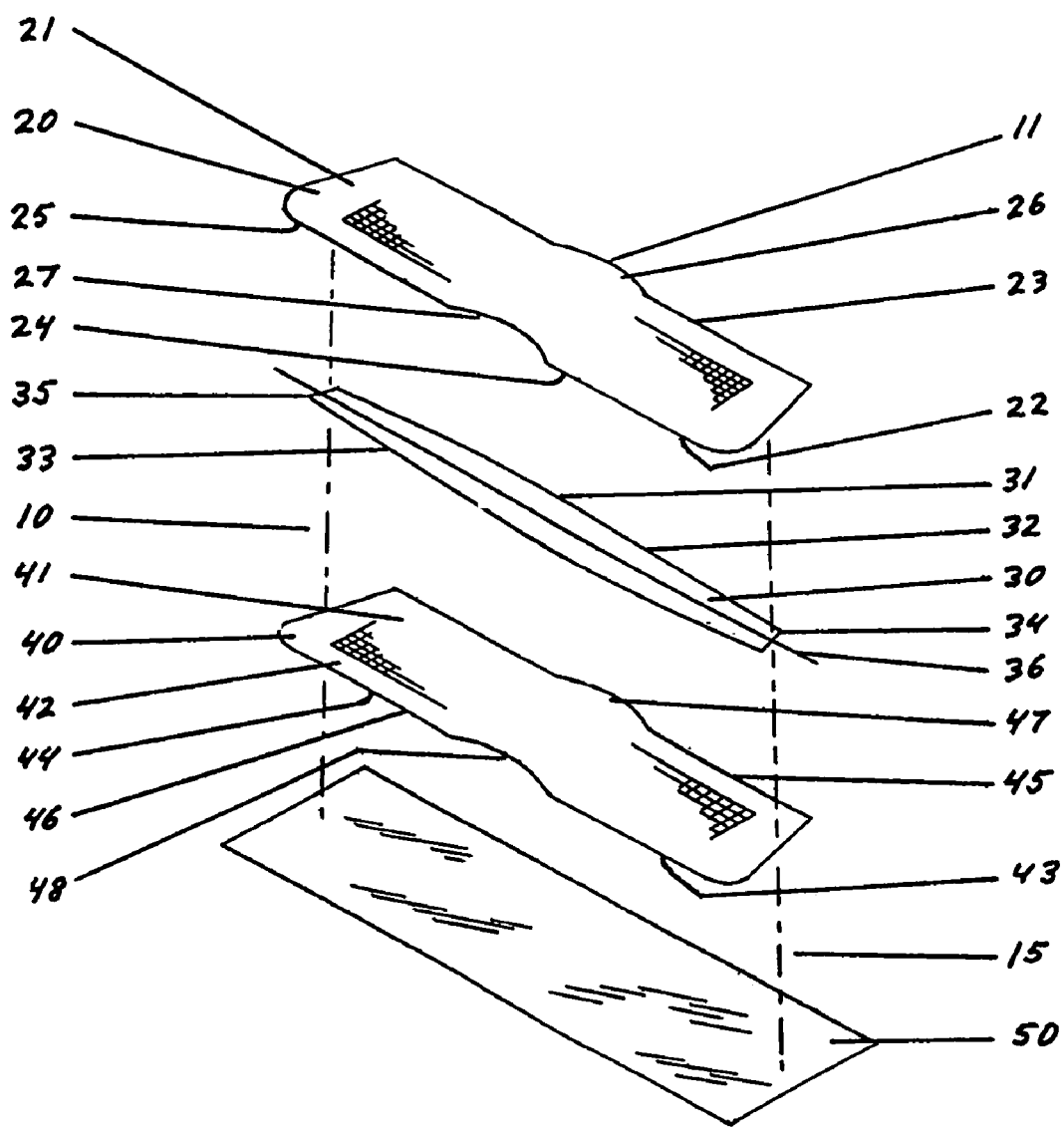
FIG. 2 is an exploded perspective top view of the components making up the dilator.

Referring to FIG. 2, the nasal dilator 10 is made up of several layers. The first layer is the top cover 20 which is made from a non-woven polyester fabric or equal which is usually tan in color on the top surface 21. The top surface 21 of the top cover 20 can be dyed in any color or imprinted with a brand logo. The top cover 20 also has a bottom surface 22 which is coated with a 3 mils acrylic hypoallergenic medical grade pressure-sensitive type adhesive 25 or equal. The adhesive 25 covers the entire bottom surface 22 of the top cover 20.

The top cover 20 has two parallel sides 23 and 24 which run over the length of the top cover 20 with the exception of a 0.5-inch wide section at the center 11 of the dilator 10. On one side 23 of the top cover 20, there is a convex protrusion 26 which is designed to indicate the proper orientation of the strip when it is in use. On the opposite side 24 of the top cover 20, there is a concave indent 27 that matches the shape of the convex protrusion 26, so that over the entire span of the top cover 20, the width measured across adjacent points on sides 23 and 24 is constant.

The second layer is the resilient band 30, a plastic layer, which is made from a clear polyester sheet which is about 0.010 inch to 0.015 inch thick, depending on the required strength of the nasal dilator 10. The thickness selected of the resilient band 30 is constant over the entire length of the resilient band 30, so the nasal dilator 10 can be manufactured in a converting process. The width of the resilient band 30 is greatest at the center 31 where the nasal dilator 10 passes over the bridge of the nose 71. The two sides 32 and 33 of the resilient band 30 curve towards each other as the distance from the center 31 of the resilient band 30 is increased. This reduction of the width of the resilient band 30 causes a reduction of the spring rate in the resilient band 30 over the span from the center 31 to each of the ends 34 and 35 of the resilient band 30. The width at the center 31 of the resilient band 30 is less than half of the width of the top cover 20, and the width of the resilient band 30 at each of the ends 34 and 35 is approximately half of the width of the center 31.

In a preferred embodiment, the sides 32 and 33 of the resilient band 30 between the center 31 and the respective ends 34 and 35 are curved over the length of the strip and preferably symmetrical in relation to the longitudinal center line 36 of the resilient band 30. Other curves for sides 32 and 33 are possible as long as the maximum width of the resilient band 30 is at the center 31 and the spring rate is reduced as the distance from the center 31 is increased until reaching ends 34 and 35. To attain the desired force distribution, the radius of curvature of the sides 32 and 33 of the resilient band 30 is greater than 1.5 inches. In addition, the thickness of the resilient band 30 is 3% or greater than the width of the resilient band at the longitudinal center line 36. This ratio increases as the distance from the center 31 is increased, and the width of the resilient band decreases until reaching ends 34 and 35.

The third layer is the cushion layer 40 which is designed to prevent direct contact between the resilient band 30 and the skin of the user. The cushion layer 40 is the same shape as the top cover 20 and is made from woven polyester or equal. The cushion layer 40 has a top surface 41 which has a 1.5 mils acrylic hypoallergenic medical grade adhesive 42 and a bottom surface 43 which has a 3.0 mils acrylic hypoallergenic medical grade adhesive 44.

The cushion layer 40 has two parallel sides 45 and 46 which match the two parallel sides 23 and 24 of the top cover 20. The cushion layer 40 also has a convex protrusion 47 and a concave indent 48 which match the convex protrusion 26 and concave indent 27 of the top cover 20.

The fourth layer of the nasal dilator 10 is a release liner 50. The release liner 50 covers the adhesive 44 on the bottom surface of the cushion layer 40 until the nasal dilator 10 is ready for use. The release liner 50 has sufficient surface area to hold one or more nasal dilators 10. The sides 23 and 24 of the top cover 20 are designed to be mirror images of each other. This allows a single cut of the converting machine to separate adjacent nasal dilators 10 so the release liner 50 sheet may have from four to six nasal dilators 10 on a single sheet. This maximizes the efficiency of the converting manufacturing process.

The nasal dilator 10 is a truss assembly 15 which includes the top cover 20 which has the resilient band 30 attached at the center of the bottom surface 22 by the adhesive 25. The bottom surface 22 extends beyond the edges of the resilient band 30 so the cushion layer 40 with its adhesive 42 on the top surface 41 can be laminated to the bottom side 37 of the resilient band 30 and to the bottom surface 22 of the top cover 20 which extends beyond the sides 32 and 33 of the resilient band 30.

The nasal dilator 10 truss assembly 15 is normally in a planar state when it is removed from the release liner 50 and has no stresses. When the nasal dilator 10 is bent over the bridge 71 of the nose 70 and the ends 12 and 13 are engaged with the lateral wall 72 of the nasal passage, then the stresses introduced in the resilient band 30 of the truss assembly 15 cause the ends 12 and 13 of the nasal dilator 10 to pull outwardly on the lateral wall 72 to improve the breathing of the user.

The nasal dilator 10 can also be provided as a clear nasal dilator 10. In this design the top cover 20 is made from a 3 mil polyethylene with the bottom surface 22 coated with 2 mils acrylic hypoallergenic medical grade adhesive 25. The resilient band 30 is made from the clear polyester used in the tan nasal dilator 10 and the cushion layer 40 is made from 3 mil polyethylene with both the top surface 41 and the bottom surface 42 coated with 2 mils acrylic hypoallergenic medical grade adhesive 41 and 42.

Figure 3:
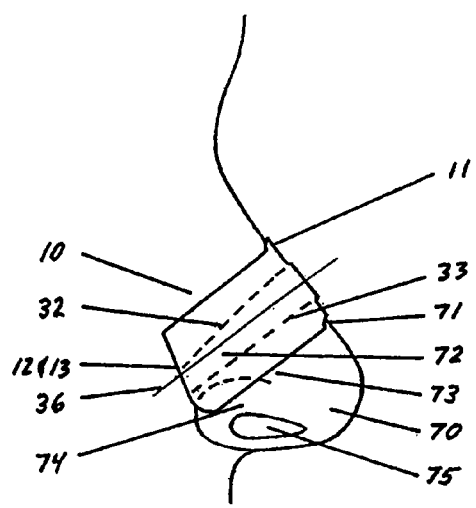
FIG. 3 is a side view of the dilator on the nose with the asymmetrical resilient band sloped toward the nostril.
Figure 4:
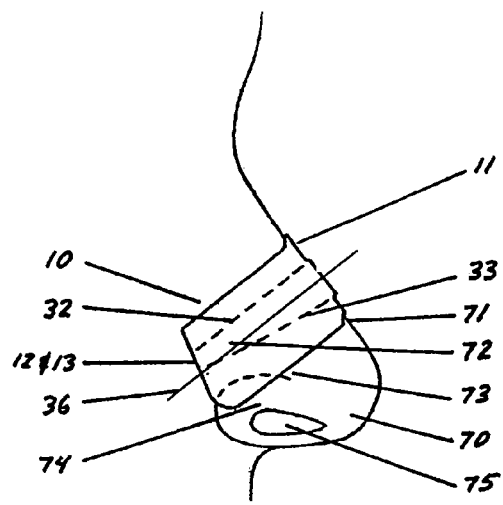
FIG. 4 is a side view of the dilator on the nose with the asymmetrical resilient band sloped away from the nostril.

FIGS. 3 and 4 show another embodiment of the resilient band 30 which is part of the nasal dilator 10. In FIG. 2, the resilient band 30 is symmetrical to the longitudinal centerline 36 of the resilient band 30. This is achieved by using identical curves for sides 32 and 33 between the center 31 and the ends 34 and 35 of the resilient band 30. In FIGS. 3 and 4, the sides 32 and 33 have different curves and are not symmetrical with respect to the longitudinal centerline 36 of the resilient band 30. The concept of using a reduction of the width in the resilient band 30 that causes a reduction of the spring rate in the resilient band 30 can be used in nasal dilator 10 with one or more parallel resilient bands that extend parallel to the longitudinal center line 36 of the nasal dilator 10.

Figure 5:
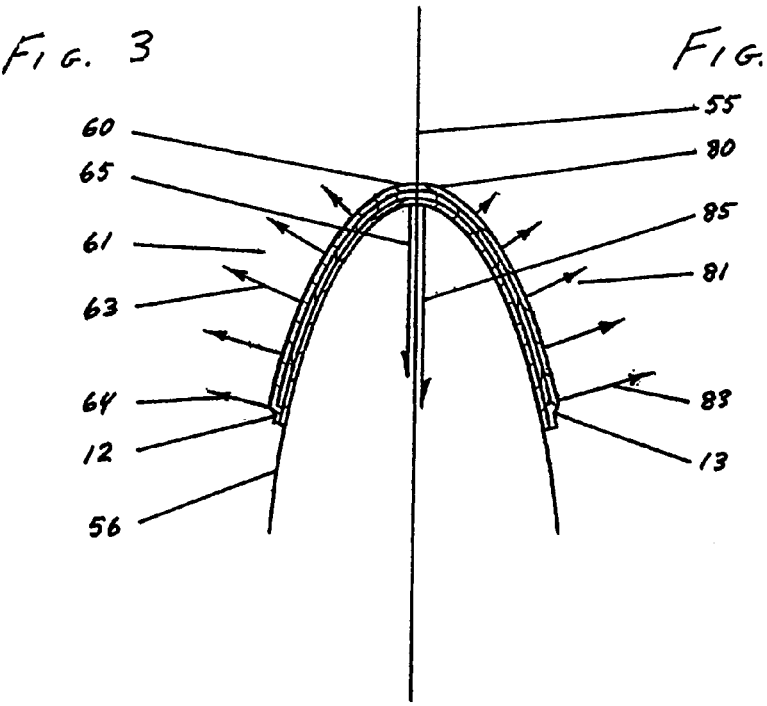
FIG. 5 is a drawing showing the force vectors of the dilator in this invention compared to the force vectors in the Iriarti dilator.

The use of a resilient band 30 with a decreasing spring rate in a nasal dilator has a positive effect on the nasal dilator performance. FIG. 5 shows a comparison of the performance of a nasal dilator 10 with a decreasing spring rate 60 on the left side of the vertical centerline 55 and a nasal dilator 10 with a constant spring rate 80 on the right side of the vertical centerline 55. The nasal dilator 10 is shown bent over an elliptical surface 56 which represents the skin 76 of the user's nose 70.

The nasal dilator 10 with the decreasing spring rate 60 has a series of vectors 61 pulling out on the elliptical surface 56. Vectors 61 which are further away from the vertical centerline 55 increase to vector 63. Then they begin to decrease to vector 64 at the end 12 of the nasal dilator 10. The vectors 61 on the side with the decreasing spring rate 60 cause the lateral wall 72 to be pulled up and out at the center of the nasal passage 75, which improves the air flow in the nasal passage 75. A reactive vector 65 provides an opposing force to vectors 61.

On the side with a nasal dilator 10 with a constant spring rate 80 there are a series of vectors 81 pulling out on the elliptical surface 56. As the vectors 81 move away from the vertical centerline 55, they increase until the last vector 83. This means that the pull on the lateral wall 72 is outward and that the maximum vector 83 is pulling out on the lateral wall 72 at the edge of the nasal passage 75. Although air flow is improved, the nasal dilator 10 with the decreasing spring rate 60 provides better performance because it opens the lateral wall 72 adjacent to the center of the nasal passage 75 where the maximum air volume flows. Also the reactive vector 85 is greater than the reactive vector 65 for the decreasing spring rate 60 nasal dilator 10, which renders the constant spring rate 80 nasal dilator 10 is less comfortable for the user.

The description of the preferred embodiment described herein is not intended to limit the scope of the invention, which is properly set out in the claims.

What is claimed is:

1. A nasal dilator capable of introducing separating stresses in nasal outer wall tissues comprising:
   a truss of a single body with a resilient member secured therein having a pair of spaced-apart end surfaces which, if forced toward one another from initial positions to substantially reduce direct spacing therebetween by a spacing reducing force external to said truss, results in restoring forces in said truss tending to restore said direct spacing between said end surfaces;
   the resilient member being symmetrical with respect to a centerline of the resilient member, the resilient member having longitudinal sides which converge from the centerline to respective ends of the resilient member for a constantly varying spring rate which diminishes from the centerline to said ends; and
   engagement means adhered to said end surfaces and capable of engaging exposed surfaces of nasal outer wall tissues sufficiently to remain so engaged against said restoring forces.

2. A nasal dilator according to claim 1 wherein the resilient member is asymmetrical relative to a long axis of the truss.

3. A nasal dilator according to claim 1 wherein the resilient member is symmetrical relative to a long axis of the truss.

4. A nasal dilator according to claim 1 including a cushioning layer with adhesive on both sides to prevent direct contact of the resilient band and the skin on the nose.

5. A nasal dilator according to claim 1 wherein the sides of the resilient member have a radius of curvature greater than 1.5 inches.

6. A nasal dilator according to claim 1 including at least two resilient members arranged side-by-side.

7. A nasal dilator according to claim 6 wherein the top cover, the resilient band, and the cushion layer are fabricated of transparent materials.

8. A nasal dilator according to claim 6 wherein the top cover is colored.

9. A nasal dilator according to claim 6 wherein the top cover includes at least one of printing, a logo, and a visual design.

10. A nasal dilator according to claim 6 including a release liner protecting the adhesive on the bottom surface of the cushion layer.

11. A nasal dilator according to claim 6 wherein the resilient band is asymmetrical relative to its longitudinal centerline.

12. A nasal dilator according to claim 1 wherein a thickness of the resilient member is 3% or greater compared to a width of the resilient member.

13. A nasal dilator according to claim 1 including a convex protrusion and a concave indent defined by respective sides of the dilator to allow a user to properly install the dilator.

14. A nasal dilator according to claim 13 wherein the convex protrusion and concave indent are designed so that the width of the dilator is constant over its entire length.

15. A nasal dilator for preventing the outer wall tissue of nasal passages of a nose from drawing in during breathing comprising:
   a unitary truss member having a normally substantially planar state, the unitary truss member including:
   a top cover which has an adhesive on a bottom surface;
   a resilient band engaged with the bottom surface having a constant thickness over its length and longitudinal sides which converge from a mid-point of the band to respective ends of the band; and
   a cushion layer which adhesively engages a bottom of the resilient band, peripherally extends past the resilient band, and adhesively engages the bottom surface of the top cover, and adhesive on a bottom of the cushion layer which engages the skin on the nose.

16. A nasal dilator for preventing the outer wall tissue of nasal passages of a nose from drawing in during breathing comprising:
   an elongated unitary truss member having a longitudinal axis, opposing ends, a centerline midway between the ends which is perpendicular to the longitudinal axis, and a normally substantially planar state, the unitary truss member including:
   a top cover which has an adhesive on a bottom surface thereof
   an elongated resilient band engaged with the bottom surface, extending in a longitudinal direction of the truss member, and having a constant thickness and sides which converge from a center of the resilient band to respective ends thereof; and
   a cushion layer defining a lowermost portion of the truss member, covering the resilient band, and including an adhesive on a bottom surface of the cushion layer for engaging skin tissue on the nose to secure the truss member to the nose.

17. A nasal dilator capable of introducing separating stresses in nasal outer wall tissue comprising:

a truss member with a plurality of resilient members secured therein, each resilient member having spaced-apart ends which, when forced toward one another from an initial, relaxed position of the truss to substantially reduce direct spacing between the end surfaces by a force external to said truss, generate restoring forces in the truss tending to return the truss to its initial relaxed position;

the plurality of resilient members having long axes which generally extend in the direction of a long axis of the truss, at least one of the resilient members having a constant thickness over its length and sides which converge from a center of the resilient members to respective ends thereof so that the plurality of resilient members collectively have a spring rate which continuously diminishes from the center to said ends; and adhesive on at least the end surfaces for engaging exposed surfaces of nasal outer wall tissues sufficiently to remain engaged while the restoring forces are active.

18. A nasal dilator according to claim 17 wherein the truss member has longitudinal sides which are configured so that a width of the dilator is constant over its entire length.

19. A nasal dilator according to claim 18 wherein the longitudinal sides respectively include a convex protrusion and a concave indent.

20. A nasal dilator according to claim 17 wherein the resilient members are parallel to each other.

21. A nasal dilator according to claim 17 wherein the resilient members are angularly inclined relative to the long axis of the truss.

* * * * *